US 6,689,907 B1

(12) United States Patent
Labat

(10) Patent No.: US 6,689,907 B1
(45) Date of Patent: Feb. 10, 2004

(54) PROCESS FOR THE MANUFACTURE OF MERCAPTOCARBOXYLIC ACIDS FROM UNSATURATED CARBOXYLIC ACIDS

(75) Inventor: Yves Labat, Pau (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/713,189

(22) Filed: Nov. 16, 2000

Related U.S. Application Data

(63) Continuation of application No. 09/091,175, filed as application No. PCT/FR96/01970 on Dec. 10, 1996.

(30) Foreign Application Priority Data

Dec. 11, 1995 (FR) .............................. 95 14638

(51) Int. Cl.[7] ..................... C07C 53/00; C07C 315/00
(52) U.S. Cl. ...................................... 562/512; 562/594
(58) Field of Search ............................... 562/512, 594

(56) References Cited

U.S. PATENT DOCUMENTS

| 3,517,058 A | | 6/1970 | Thoma et al. | |
|---|---|---|---|---|
| 3,840,586 A | * | 10/1974 | Chiba et al. | 562/512 |
| 3,927,085 A | | 12/1975 | Zengel et al. | |
| 4,490,307 A | * | 12/1984 | Klenk | 562/512 |
| 5,008,432 A | * | 4/1991 | Roberts | 558/436 |
| 5,157,147 A | * | 10/1992 | Chisholm et al. | 560/147 |
| 5,391,820 A | * | 2/1995 | Woodbury et al. | 562/512 |

FOREIGN PATENT DOCUMENTS

| FR | 1485206 | | 9/1967 |
|---|---|---|---|
| GB | 639679 | | 7/1950 |
| GB | 670702 | | 4/1952 |
| GB | 1358019 | | 6/1974 |
| JP | 07228568 | * | 8/1995 |

OTHER PUBLICATIONS

International Search Report dated Mar. 26, 1997.
37 Collection of Czechoslovak Chemical Communications, "Synthese der Thioapfelsaure", A. Emr, et al., vol. 21, No. 6, 1956, Prague C.S., pp. 1651–1653.

* cited by examiner

*Primary Examiner*—Alan L. Rotman
*Assistant Examiner*—Taylor V Oh
(74) *Attorney, Agent, or Firm*—Smith, Gambrell & Russell, LLP

(57) ABSTRACT

A mercaptocarboxylic acid of formula (I) is prepared by reacting an unsaturated carboxylic acid of formula (II) with a hydrosulphide of formula ASH, A being an alkali metal cation or a cation $NR^3R^4R^5R^{6+}$, $R^3$ to $R^6$ each representing H or a hydrocarbon radical, or of formula $Q(SH)_2$, Q being an alkaline-earth metal cation, by acidifying the resulting reaction medium in order to obtain the desired compound (I). According to the present invention, the reaction is carried out with a supply of $H_2S$ other than that supplied by the neutralization of the acid (II). In particular, $H_2S$ is introduced into the medium by a direct external supply. $H_2S$ can also be produced in situ by reacting the hydrosulphide with at least one acid introduced into the medium.

The compound (I) is obtained with a very good selectivity.

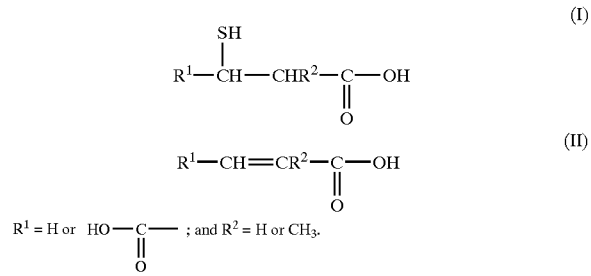

14 Claims, No Drawings

PROCESS FOR THE MANUFACTURE OF MERCAPTOCARBOXYLIC ACIDS FROM UNSATURATED CARBOXYLIC ACIDS

CONTINUING APPLICATION DATA

This is a continuation under 37 C.F.R. §1.53 (b) of pending U.S. patent application Ser. No. 09/091,175 filed Apr. 9, 1999, which in turn is a 371 of PCT application No. PCT/FR96/01970 having the filing date of Dec. 10, 1996. All of these applications are relied upon and incorporated herein by reference in their entirety.

FIELD OF THE INVENTION

The present invention relates to a new process for the manufacture of mercaptocarboxylic acids represented by the formula (I):

$$R^1-\underset{\underset{SH}{|}}{CH}-CHR^2-\underset{\underset{O}{\|}}{C}-OH \quad (I)$$

in which:

$R^1$ represents hydrogen or $$HO-\underset{\underset{O}{\|}}{C}-\ ;$$

and $R^2$ represents hydrogen or methyl.

BACKGROUND OF THE INVENTION

These mercaptocarboxylic acids are useful as intermediates for synthesis into the esters (for example with 2-ethylhexanol, pentaerythritol) used either to obtain tin salts (stabilizers for PVC), or as hardening or modifying agents for epoxide resins (adhesives) and for polyurethanes (optical glasses). Mercaptopropionic acid can also serve to modify acrylic polymers (paint, paper industry).

Various routes are known for producing mercaptocarboxylic acids:

(1) One of these routes consists in reacting halogenated saturated carboxylic acids with alkali metal hydrosulphides and under an $H_2S$ pressure. This route is widely described in the literature for thioglycolic acid from monochloroacetic acid, and for mercaptopropionic acid from 3-chloropropionic acid (see American patent U.S. Pat. No. 3,927,085). It is known that this reaction is very selective if the operating conditions are well chosen. However, the stoichiometry of the reaction requires the use of 2 mol of alkali metal hydrosulphide per mol of chlorinated carboxylic acid and the consequent formation of 2 mol of inorganic salt to be removed in the aqueous effluent.

(2) Reactions for opening the lactone rings by alkali metal hydrosulphides have also been proposed; thus, the formation of β-mercaptopropionic acid from β-propiolactone and NaSH is described in British Patent No. 639 679. It should be indicated here that propiolactone is not commercially available.

(3) The preparation of 3-mercaptopropionic acid can also be carried out from widely available raw materials such as unsaturated organic acids and, in particular, the acrylic derivatives.

The reaction of $H_2S$ in a basic medium or of alkali metal hydrosulphides makes it possible to obtain as an intermediate, starting with acrylonitrile, mercaptopropionitrile which can be subsequently hydrolyzed to 3-mercaptopropionic acid.

However, very special conditions should be observed in order to avoid the very easy reaction of the mercaptopropionitrile formed with the unreacted acrylonitrile. The thiodipropionitrile sulphide is indeed very easy to form and it is then necessary to subsequently carry out a sulphohydrolysis of the sulphide to mercaptan, thereby complicating the preparation process.

Moreover, in addition to going via toxic and unstable products (mercaptopropionitrile), this process has the disadvantage that 2 mol of salt will be further formed per mol of 3-mercaptopropionic acid.

Another possibility is that consisting of using, as raw material, methyl acrylate, and to form, by reaction with $H_2S$, methyl mercaptopropionate, which, by hydrolysis, will lead to 3-mercaptopropionic acid. This route is economically unattractive because it occurs in two stages, with the loss of one mol of methanol.

A direct route for preparing mercaptopropionic acid consists in starting with acrylic acid, which is a cheap raw material. The reaction of acrylic acid in liquid phase, with a large excess of $H_2S$ in the presence of an organic base as catalyst, is not easy to carry out. The other technique, consisting in reacting acrylic acid with $CS_3Na_2$, makes it possible to enhance the selectivity in relation to mercaptopropionic acid and to carry out the procedure without an $H_2S$ pressure. Unfortunately, the use of $CS_2$ and of methanol as cosolvent makes the process cumbersome, especially with regard to the treatment of effluents.

GB-A-670 702 describes, in its example I, the following reaction:

$$NaSH\ +\ NaO_2C-CH=CH-CO_2Na\ \longrightarrow$$

$$HO_2C-\underset{\underset{SH}{|}}{CH}-CH_2-CO_2H$$

In fact, thiodisuccinic acid $$S[\underset{\underset{COOH}{|}}{CH}-CH_2-COOH]_2,$$

which undergoes sulphohydrolysis to mercaptan because of the basic pH, is first prepared. In other words, generally speaking a sulphide is first formed, which sulphide undergoes sulphohydrolysis to mercaptan according to the reaction scheme:

$$ASH\ +\ R^1-CH=CR^2-COOH\ \longrightarrow\ S[\underset{\underset{R^1}{|}}{CH}-\underset{\underset{R^2}{|}}{CH}-COOH]_2$$

$$S[\underset{\underset{R^1}{|}}{CH}-\underset{\underset{R^2}{|}}{CH}-COOH]_2\ \xrightarrow{+\ ASH}\ 2\ R^1-\underset{\underset{SH}{|}}{CH}-CHR^2-COOH$$

A, $R^1$, $R^2$ being as defined below.

Applicant has, moreover, experimentally confirmed this reaction scheme. The article in Collection of Czechoslovak Chemical Communications, Vol 21, No. 6, 1956, Prague CS, pages 1651–1653 presents what is described in GB-A-670 702.

GB-A-1 358 019 describes a process for the preparation of β-mercaptopropionic acid by reaction of acrylic acid with MSH where M=ammonium group or alkali or alkaline-earth metal in the presence of carbon disulphide $CS_2$. $CS_2$ plays the role of coreagent and prevents the sulphide from being formed:

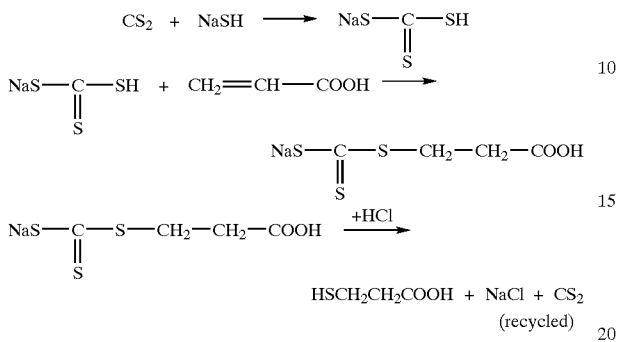

In accordance with the documents which have just been cited, the aim is to obtain a better selectivity in relation to mercaptocarboxylic acids and to avoid the formation of sulphides. In fact, the aim would be to avoid the formation of sulphides by reaction of the mercaptan already formed and the nonconverted acrylic compound:

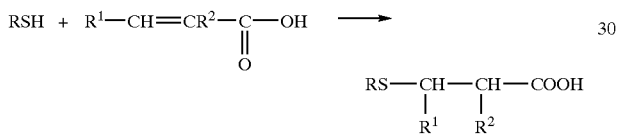

with

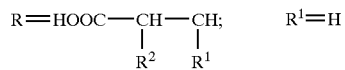

or HOOC—and $R^2$=H or $CH_3$.

DESCRIPTION OF THE INVENTION

The present invention is essentially centred on the beneficial effect of the solubility of $H_2S$ in the reaction medium which promotes the formation of mercaptan. In accordance with the present invention, carrying out the procedure with a supply of $H_2S$ leads directly to the desired mercaptan, the sulphohydrolysis of the sulphide

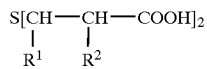

becoming impossible under these conditions.

According to the invention, hydrosulphides are therefore reacted with unsaturated carboxylic acids, according to the following overall reaction (case where the hydrosulphide is represented by ASH):

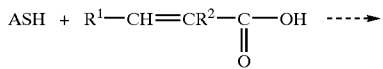

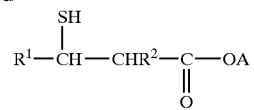

A=ammonium or alkali metal cation;
$R^1$=H or

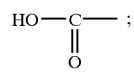

and
$R^2$=H or $CH_3$
which is, in fact, the sum of the following two reactions:

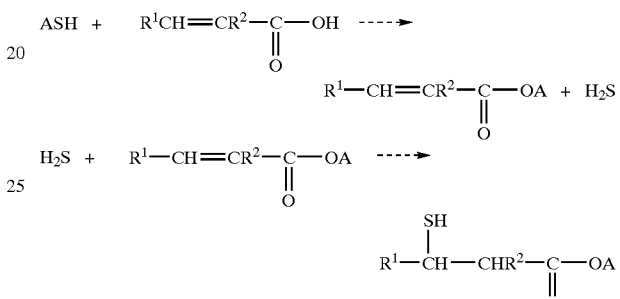

It was surprising to observe that, under the abovementioned conditions, the mercaptan formed reacts weakly with the unsaturation of the acid $R^1$—CH=$CR^2$—COOH, whereas the reaction of formation of the mercaptan is itself highly favoured. This results in very good selectivities in relation to the desired compound of formula (I) which are higher than those of known processes.

The subject of the present invention is therefore a process for the manufacture of a mercaptocarboxylic acid represented by the formula (I) as defined above, according to which an unsaturated carboxylic acid of formula (II):

(II)
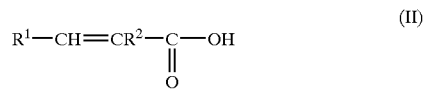

in which $R^1$ and $R^2$ are as defined above, is reacted with a hydrosulphide of formula ASH, A being an alkali metal cation or a cation $NR^3R^4R^5R^{6+}$, $R^3$ to $R^6$ each representing H or a hydrocarbon radical, or of formula $Q(SH)_2$, Q being an alkaline-earth metal cation, and the resulting reaction medium is acidified in order to obtain the desired compound (I), characterized in that the reaction is carried out with a supply of $H_2S$ other than that supplied by the neutralization of the acid (II).

The starting acid (II) is chosen especially from acrylic acid, methacrylic acid, maleic acid and fumaric acid.

In general, the reaction according to the invention may be carried out in an aqueous medium, but an enhancement of the selectivity can be obtained using an aqueous-alcoholic or a purely alcoholic medium. This alcoholic medium, or the alcohol fraction of the aqueous-alcoholic medium, is formed, for example, by methanol, propanol, isopropanol or a mixture of these alcohols.

An important parameter which governs the selectivity in relation to mercaptocarboxylic acid (I) is the $H_2S$/acid (II)

molar ratio in solution. The higher the $H_2S$ concentration in solution, the better the selectivity in relation to the acid (I). If the procedure is carried out without a supply of $H_2S$ other than that supplied by the neutralization of the acid (II), this ratio is 1. If $H_2S$ is supplied to the reaction system, its solubility in the reaction medium depends on several physical factors:

- dilution of the medium (true $H_2S$/acid (II) molar ratio in solution will be higher);
- use of an alcoholic or aqueous-alcoholic medium;
- increase in the $H_2S$ pressure; and
- to a lesser degree, reduction in the temperature; as well as on the $H_2S$/acid (II) ratio in solution.

To increase this ratio, as is envisaged by the present invention, $H_2S$ may be introduced into the medium by a direct external supply and/or $H_2S$ may be produced in situ by reacting the hydrosulphide with at least one acid introduced into the medium, in accordance with the following reaction (with ASH):

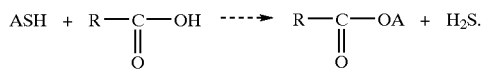

This acid may be chosen from the saturated organic acids of formula RCOOH, R representing especially a $C_1$–$C_{18}$ alkyl residue capable of carrying substituents such as halogens, and from inorganic acids.

The acid RCOOH is advantageously chosen from acetic acid, propionic acid and 3-chloropropionic acid. In the case where it is desired to obtain 3-mercaptopropionic acid, the procedure is advantageously carried out in the presence of 3-chloropropionic acid which will itself lead to the desired 3-mercaptopropionic acid, in accordance with the following reactions:

2ASH+Cl—$CH_2CH_2$—COOH→HS—$CH_2$—$CH_2$—COOA+$H_2S$ +ACl

ASH+$CH_2$=CH—COOH→HS—$CH_2$—$CH_2$—COOA

At least one inorganic acid, such as HCl, $H_2SO_4$, and the like may also be used in place of the organic acid.

The pH should advantageously be from 6.5 to 8, and preferably from 6.8 to 7.5 in the reaction medium under an $H_2S$ pressure so as to avoid nucleophilic attack of the $^-$S—Y—$CO_2^-$ species (Y=$CHR^1$—$CHR^2$) on the double bond to give the sulphide.

In accordance with another characteristic of the process according to the invention, the procedure is advantageously carried out under an $H_2S$ pressure of at least 8 bar, especially from 8 to 30 bar. As regards the reaction temperature, it is advantageously between 10 and 150° C. In the case of the preparation of 3-mercaptopropionic acid, this temperature is generally from 20 to 100° C.

The acid (II) concentration, expressed in moles per liter of solvent (water or alcohol or water+alcohol) is generally between 0.5 and 4.

The hydrosulphide ASH or $Q(SH)_2$ may be prepared separately and injected into the reactor, or may be formed in situ, at least in part, by reaction in an aqueous or alcoholic or aqueous-alcoholic medium of $H_2S$ with AOH or $Q(OH)_2$, A and Q being as defined above. Thus, the hydrosulphide may be obtained by reaction of $H_2S$ with sodium hydroxide, potassium hydroxide, lime, amines and ammonium hydroxide.

One of the advantages of the process in accordance with the present invention is that it can be applied in existing industrial plants already optimized for the synthesis of mercaptocarboxylic acids from chlorinated carboxylic acids (thioglycolic acid for example).

It should also be emphasized that the process of the invention is carried out in an aqueous or aqueous-alcoholic or alcoholic medium without using $CS_2$ and without the process being carried out in a large excess of $H_2S$. Another economic advantage is that only one molecule of salt per molecule of mercaptocarboxylic acid is formed if $H_2S$ from an external source is used, in contrast to processes starting with halogenated carboxylic acids which, during their conversion to mercaptans, form 2 mol of salt which has to be removed.

EXAMPLES

The following examples further illustrate the present invention, without however limiting its scope.

EXAMPLE 1

Preparation of 3-mercantopropionic Acid 440 g of an aqueous solution containing 12.5 g of $NH_3$, that is to say 0.73 mol, are introduced into a 2-liter thermostatted autoclave.

$H_2S$ is introduced into the autoclave to maintain the pressure constant at 25 bar for the duration of the experiment. The temperature is raised to 40° C. and 48 g of acrylic acid, that is to say 0.66 mol, are introduced into the reactor by means of a pump.

The experiment is continued for an additional one hour at 40° C. at 25 bar of $H_2S$. The reactor is then cooled, the excess $H_2S$ is driven off, the medium is acidified, the aqueous solution is extracted with isopropyl ether, this solvent is evaporated off, and the crude 3-mercaptopropionic acid (0.528 mol) is obtained, that is to say 62 g of a product at 90% purity, which is then distilled under vacuum. Yield: 80%

EXAMPLES 2a, 2b and 3 to 7

The procedure is carried out as in Example 1, except that the acrylic acid concentration and/or the $H_2S$ pressure is varied or that 3-chloropropionic acid is introduced or otherwise and that the procedure is carried out in a methanolic medium, the mean temperature being 40° C. (temperature range=20–60° C.).

The results are presented in the following table.

TABLE

| Example | Number of moles of acrylic acid/litre of solvent (water or methanol) | Acrylic acid/3-chloropropionic acid molar ratio | $H_2S$ pressure (bar) | Medium | 3-mercapto-propionic acid yield |
|---|---|---|---|---|---|
| 1 | 1.5 | without 3-chloropropionic acid | 25[1] | aqueous | 80 |
| 2a | 1 | without 3-chloropropionic acid | 24[1] | aqueous | 83 |
| 2b | | | 23[2] | aqueous | 82 |
| 3 | 2 | without 3-chloropropionic acid | 20[1] | aqueous | 71 |

TABLE-continued

| Example | Number of moles of acrylic acid/litre of solvent (water or methanol) | Acrylic acid/3-chloropropionic acid molar ratio | $H_2S$ pressure (bar) | Medium | 3-mercapto-propionic acid yield |
|---|---|---|---|---|---|
| 4 | 2.5 | without 3-chloropropionic acid | 25$^{(1)}$ | methanolic | 87.5 |
| 5 | 2.5 | 1 | 18 | aqueous | 82 |
| 6 | 2 | 2 | 20 | aqueous | 81 |

$^{(1)}$The $H_2S$ pressure is partly regulated by means of an external supply of $H_2S$
$^{(2)}$The $H_2S$ pressure is obtained only by the reaction of organic acids and $NH_4SH$. Here, the procedure is carried out with an acrylic acid/acetic acid molar ratio of 1.

EXAMPLE 8

Preparation of Thiomalic Acid 12 mol of sodium hydroxide is introduced into about 1900 g of water in a 2-liter autoclave. The medium is saturated with $H_2S$ and the pressure is maintained at 10 bar. Maleic acid previously dissolved in water, in an amount of 2 mol (232 g) in 365 g of water, is introduced into the autoclave by a pump. The temperature is raised to 120° C. and maintained for 4 hours, with stirring.

After cooling the reactor, acidification and stripping, thiomalic acid is obtained in solution, in an amount of 1.50 mol, that is to say 225 g. This corresponds to a thiomalic acid yield of 75% relative to the maleic acid.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process for the manufacture of a mercaptocarboxylic acid of formula (I):

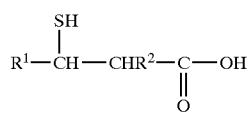   (I)

in which:

$R^1$ represents hydrogen or

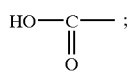 ;

and $R^2$ represents hydrogen or methyl;
comprising the steps of reacting in a reaction medium (a) an unsaturated carboxylic acid of formula (II):

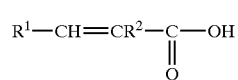   (II)

in which $R^1$ and $R^2$ are as defined above, and (b) a hydrosulphide of formula ASH, A being an alkali metal cation or a cation $NR^3R^4R^5R^{6+}$, $R^3$ to $R^6$ each representing H or a hydrocarbon radical, or of formula $Q(SH)_2$, Q being an alkaline-earth metal cation; wherein the reaction medium is selected from the group consisting of an aqueous medium, an aqueous-alcoholic medium and an alcoholic medium, introducing a supply $H_2S$ into the reaction medium, wherein the $H_2S$ is introduced into the medium by a direct external supply or is produced in situ by reacting the hydrosulphide with at least one acid introduced into the medium; and acidifying the reaction medium to obtain the desired compound (I);

wherein the reaction is carried out in the reaction medium without $CS_2$, further wherein the reaction medium has a pH of from 6.5 to 8.

2. Process according to claim 1, wherein the acid introduced into the medium is selected from the group consisting of (i) saturated organic acids of formula RCOOH, R representing a $C_1$–$C_{18}$ alkyl residue optionally carrying substituents including at least one halogen, and (ii) inorganic acids.

3. Process according to claim 2, wherein the acid is selected from the group consisting of acetic acid, propionic acid, and 3-chloropropionic acid.

4. Process according to claim 1, wherein the procedure is carried out under an $H_2S$ pressure of at least 8 bar.

5. Process according to claim 1, wherein the reaction is carried out at a temperature of between 10 and 150° C.

6. Process according to claim 1, wherein the alcoholic medium or the alcohol fraction of the aqueous-alcoholic medium is formed by methanol, propanol, isopropanol, or by a mixture of these alcohols.

7. Process according to claim 1, wherein the starting acid (II) is selected from acrylic acid, methacrylic acid, maleic acid and fumaric acid.

8. Process according to claim 5, leading to 3-mercaptopropionic acid, wherein the reaction is carried out at a temperature of 20 to 100° C.

9. Process according to claim 1, wherein the acid (II) concentration, expressed in moles per liter of solvent, is between 0.5 and 4.

10. Process according to claim 4, wherein the pressure is from 8 to 30 bar.

11. Process according to claim 1, wherein the solvent is water, alcohol or water and alcohol.

12. Process according to claim 3 wherein the acid RCOOH is 3-chloropropionic acid when 3-mercaptopropionic acid is manufactured.

13. Process according to claim 1, wherein the reaction medium has a pH of from 6.8 to 7.5.

14. Process according to claim 1, wherein the inorganic acid is HCl or $H_2SO_4$.

* * * * *